United States Patent [19]

Iwata et al.

[11] Patent Number: 5,168,099
[45] Date of Patent: Dec. 1, 1992

[54] OPTICALLY ACTIVE ALKYLENEDIOXYBENZENE DERIVATIVES AND THEIR USE IN THERAPY

[75] Inventors: Heitaro Iwata, Ibaraki; Akemichi Baba, Nishinomiya; Toshio Matsuda, Settsu; Mitsuo Egawa, Machida; Akihiro Tobe, Yokohama, all of Japan; Kenichi Saito, Belmont, Mass.

[73] Assignee: Mitsubishi Kasei Corporation, Tokyo, Japan

[21] Appl. No.: 668,480

[22] Filed: Mar. 14, 1991

[30] Foreign Application Priority Data

Mar. 14, 1990 [JP] Japan .................... 2-63839

[51] Int. Cl.⁵ .................. A61K 31/335; C07D 319/20
[52] U.S. Cl. .................... 514/452; 549/366; 549/350; 514/450
[58] Field of Search ............... 549/366, 350; 514/452, 514/450

[56] References Cited

U.S. PATENT DOCUMENTS

| | | | |
|---|---|---|---|
| 3,324,143 | 6/1967 | Moed et al. | 549/366 |
| 3,444,210 | 5/1969 | Moed et al. | 549/366 |
| 3,681,393 | 8/1972 | Jones et al. | 549/366 |
| 4,684,739 | 8/1987 | Kikumoto et al. | 549/350 |

FOREIGN PATENT DOCUMENTS 0054304  6/1982  European Pat. Off. .

OTHER PUBLICATIONS

Mitsubishi, Chem. Abstr., vol. 100, No. 28 (1984) Abstract No. 191886j (Abstracting JP 58,219,114).

*Primary Examiner*—Nicky Chan
*Attorney, Agent, or Firm*—Wenderoth, Lind & Ponack

[57] ABSTRACT

Optically active alkylenedioxybenzene derivatives of the formula:

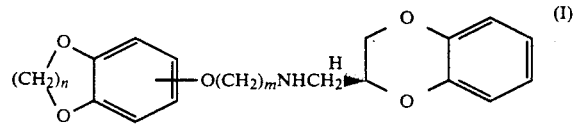

wherein m is an integer of 2–5, and n is an integer of 1–3, and acid addition salts thereof. A pharmaceutical composition containing a compound (I) or racemate, and a method of treating anxiety in a warm-blooded animal by administering the above compound (I) to said animal are also provided.

4 Claims, No Drawings

OPTICALLY ACTIVE ALKYLENEDIOXYBENZENE DERIVATIVES AND THEIR USE IN THERAPY

The present invention relates to a class of optically active alkylenedioxybenzene derivatives, the use of the derivatives as an antianxiety agent, and a pharmaceutical composition containing one of the derivatives as an essential component.

Mental anxiety has become of great interest for people due to rapid changes of social conditions and environment these days. Benzodiazepines have been known as useful as antianxiety agents for treating such mental anxiety. Recently, N-{4-[4-(2-pyrimidinyl)-1-piperazinyl]butyl}-1,1-cyclopentanediacetamide hydrochloride (known as Buspirone) has been developed as a novel antianxiety agent having a unique mode of action different from that of benzodiazepines. However, it is desired that additional compounds showing more potent antianxiety activity are provided in the medical field.

In the meanwhile, the following alkylenedioxybenzene derivatives of the formula III:

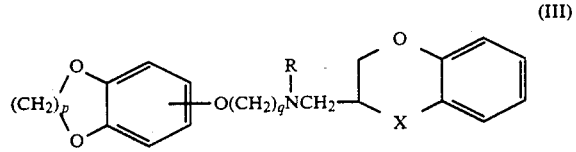

wherein R is hydrogen or lower alkyl; X is oxygen or methylene; p is an integer of 1-3; and q is an integer of 3 or 4, are known to be useful as antihypertensive agents (Japanese Patent Publication (Kokai) Nos. 108088/1982, 219114/1983 and U.S. Pat. No. 4,684,739). However, the existence of optical isomers of the above compounds (III) has not been known, and as yet, it has not been known that some of the optical isomers have antianxiety activity.

It has now been found that a special class of the optical isomers of the compounds (III) and acid addition salts thereof have an excellent antianxiety activity. Thus, the present invention is directed to a compound of the formula (I):

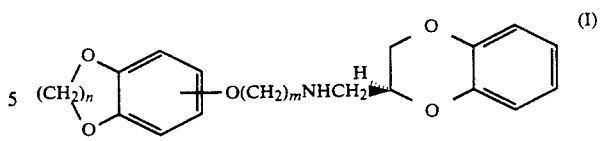

wherein m is an integer of 2–5 and n is an integer of 1–3, and acid addition salts thereof.

The present invention is also directed to a pharmaceutical composition for treating anxiety which contains as an essential component one of the compounds of the formula (II):

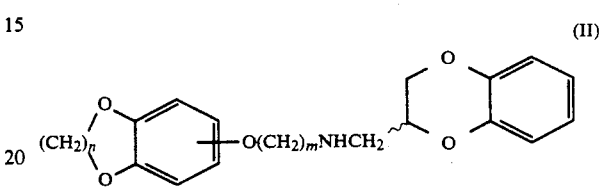

wherein m and n are as defined above, and their salts.

A further aspect of the present invention is to provide the method of treating anxiety by administrating an effective amount of one of the compounds of the formula (I) or (II) and their salts.

Preferred compounds among the compounds of the formula (I) or (II) and their salts are those in which m is 3, 4 or 5 and n is 1, 2 or 3. More preferred compounds are those in which n is 1.

Examples of the acid addition salts of the compounds (I) or (II) are those formed with an inorganic acid (e.g. hydrochloric acid, hydrobromic acid, sulfuric acid, phosphoric acid, and nitric acid), or an organic acid (e.g. acetic acid, succinic acid, adipic acid, propionic acid, tartaric acid, fumaric acid, maleic acid, oxalic acid, citric acid, benzoic acid, toluenesulfonic acid, and methanesulfonic acid).

The compounds of the formula (I) may be prepared by any one of conventional methods. For example, the compounds may be prepared according to the following reaction scheme:

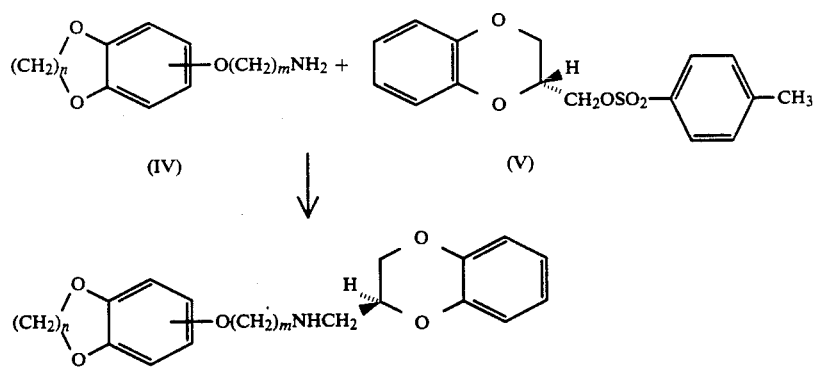

wherein m and n are as defined above.

The starting compounds (IV) may be prepared by a conventional synthetic method for primary amines, such as described in Angewandte Chemie, 80 986 (1968). Another starting material (V) may be prepared, for example, according to the teaching of Journal of Medicinal Chemistry, 20 880, (1977).

The compounds (I) of the present invention may be prepared using the starting compounds (IV) and (V) by conventional methods for preparing secondary amines. For example, the compound (V) is allowed to react with 0.5-10 molar equivalent of the compound (IV) at temperature of $-10° \sim 150°$ C. for 30 minutes $\sim$ 28 hours in the absence or presence of a solvent, such as aromatic hydrocarbons (e.g. benzene, toluene, xylene), ethers (e.g. ethylether, tetrahydrofuran (THF), dioxane), saturated hydrocarbons (e.g. n-hexane), acetonitrile, dimethylformamide, N-methylpyrrolidone, dimethylsulfoxide, and the like, and in the presence of 0.5-10 molar equivalent of an inorganic base such as potassium carbonate, sodium carbonate, potassium hydroxide, sodium hydride and the like, or an organic base such as triethylamine, pyridine, diisopropylethylamine and the like, followed by purification of the resultant product by, for instance, silica gel chromatography or recrystallization.

The compounds of the formula (II) may be easily prepared, for example in accordance with the procedures described in U.S. Pat. No. 4,684,739.

According to the present invention, the compounds (I) or (II) bind to 5-hydroxytryptamine (5-HT) receptor, particularly $5\text{-HT}_{1A}$ receptor, as illustrated in the working example described hereinafter.

It is generally known that compounds capable of binding to $5\text{-HT}_{1A}$ receptor exhibit antianxiety activity, and the following compounds are known as $5\text{-HT}_{1A}$ receptor-binding compounds: N-{4-[4-(2-pyrimidinyl)-1-piperazinyl]butyl}-1,1-cyclopentanediacetamide hydrochloride (known as Buspirone) (Naunyn-Schmiedeberg's Arch. Pharmakol., 328, 467, 1985), 2-{4-[4-(2-pyrimidinyl)-1-piperazynyl]butyl}-1,2-benzisothiazol-3-(2H) one-1,1-dioxydehydrochloride (known as Ipsapirone), and 3aα, 4β, 7β, 7aβ-hexahydro-2-{4-[4-(2-pyrimidinyl)-1-piperazinyl]butyl}-4,7-methan-1H-isoindol-1,3(2H)dione dihydrogen citrate (known as SM-3997) (Naunyn-Schmiedeberg's Arch. Pharmakol., 328, 467, 1985; Japan. J. Pharmacol., 45, 493, 1987). The compounds (I) or (II) of the invention shown $5\text{-HT}_{1A}$-binding activity similar to the above-listed known compounds and are useful as antianxiety agents.

Thus, the compounds (I) or (II) of the present invention are useful for treating or preventing acute or chronic anxiety syndrome including panic disorder optionally associated with agoraphobia, social-phobia, simple-phobia, agoraphobia, compulsive disorder (obsessinal neurosis), and stress disorder after trauma; shizophrenia; manic-depressive psychosis; hemicrania; and the like.

The compounds of the invention may be administered to patients by any one of the conventional methods. However, they are preferably administered orally or parenterally, such as subcutaneously, intravenously, or intramuscularly.

Daily dosage of the compounds may differ depending on the age, body weight or general health condition of a particular patient, presence or absence of additional active agent to be co-administered, frequency of administrations, therapeutical effect expected, and the like.

However, it may generally be 0.001-10.0 mg/kg (body weight), preferably 0.05-3.0 mg/kg (body weight). The daily dose may be administered in a single dose or in multiple doses.

The compounds of the invention are formulated in tablets, capsules, powders, solutions, elixirs for oral administration, and sterile injectable solutions or suspensions for parenteral administration. The pharmaceutical formulation of the present invention may contain nontoxic, solid or liquid, pharmaceutically acceptable carriers.

One of typical formulations of the invention is a hard or soft gelatin capsule. The formulations can also be in the form of tablets or sterile packaged powders containing an active compound together with or without adjuncts.

Capsules, tablets or powders generally contain about 5-95%, preferably about 25-90%, by weight of active compound(s) of the invention. It is preferred that the formulations are prepared in a unit dosage form so that each unit contains from about 0.5 to about 500 mg, preferably about 1 to 100 mg, of the active compound.

Specific examples of liquid carriers include sterile water, petroleum, and synthetic or natural oils from plant or animal sources, for example, peanut, soybean, mineral, or sesame oil. Preferred liquid carriers include physiological saline, an aqueous solution of dextrose or sucrose analog, and glycols such as propylene glycol or polyethylene glycol. Injectable solutions prepared using physiological saline may contain from about 0.5 to about 20% by weight, preferably, about 1 to about 10% by weight of an active ingredient.

When the formulation is in the form of a solution for oral administration, it can be a suspension or a syrup containing from about 0.5 to about 10% by weight of an active ingredient together with liquid excipients, such as flavors, syrups, pharmaceutical micels.

The following examples are illustrative only and are not intended to limit the scope of the invention in any respect.

EXAMPLE 1 5-[3-{(2S)-(1,4-Benzodioxan-2-ylmethyl) -amino}propoxy]-1,3-benzodioxol hydrochloride (Compound No. 1 in Table 1)

5-(3-Aminopropoxy)-1,3-benzodioxol (5.86 g) and (2R)-2-tosyloxymethyl-1,4-benzodioxane (Journal of Medicinal Chemistry, 20 880, 1977)(3.20 g) were dissolved in acetonitrile (100 ml), and the mixture was heated under reflux with stirring for 12 hours after addition of triethylamine (2.77 ml). After completion of the reaction, the reaction mixture was added with water and extracted with chloroform. The chloroform extract was washed with water, dried over anhydrous sodium sulfate, and concentrated. The resultant concentrate was subjected to silica gel chromatography (chloroform/ methanol) to obtain purified 5-[3-{(2S)-(1,4-benzodioxan-2-ylmethyl)amino}propoxyl]-1,3-benzodioxol (2.68 g).

The above product was dissolved in ethyl acetate, and added with 26% hydrochloric acid in isopropanol. Resultant precipitates were filtered to obtain the title compound. M.p. 212°-218° C.

$^1$H-NMR (DMSO-d$_6$) δ 9.16 (2H, m), 6.89 (5H, m), 6.63 (1H, d, J=2.4Hz), 6.37 (1H, dd, J=7.5, 2.5 Hz), 5.95 (2H, s), 4.65 (1H, m), 4.37 (1H, dd, J=12.5, 2.3 Hz), 4.02 (3H, m), 3.25 (4H, m), 2.10 (2H, m).

After amidation of the above optical isomer and racemate (prepared according to the method disclosed in U.S. Pat. No. 4,684,739), using (S)-methoxytrifluoromethyl-phenylacetic acid chloride in the presence of pyridine, both of the amides were subjected to high pressure liquid chromatography (column: Water Novapac C18). Comparative analysis of the resultant chromatogram of both compounds revealed that the optical isomer's optical density was over 99% e.e.

EXAMPLE 2 5-[4-{(2S)-(1,4-Benzodioxan-2-ylmethyl)-amino}butoxy]-1,3-benzodioxol hydrochloride (Compound No. 4 in Table 1)

The procedure in Example 1 was repeated except that 5-(4-aminobutoxy)-1,3-benzodioxol was employed rather than 5-(3-aminopropoxyl)-1,3-benzodioxol to obtain the title compound. M.p. 169°–171° C.

$^1$H-NMR (DMSO-d$_6$) δ 9.20 (2H, m), 6.89 (5H, m), 6.61 (2H, d, J=2.5 Hz), 6.35 (2H, dd, J=8.5, 2.5 Hz), 5.94 (2H, s), 4.65 (1H, m), 4.36 (1H, dd, J=11.8, 2.3 Hz), 4.05 (1H, m), 3.90 (2H, m), 3.10 (4H, m), 1.75 (2H, m).

EXAMPLE 3 5-[5-{(2S)-(1,4-Benzodioxan-2-ylmethyl)-amino)pentyloxy]-1,3-benzodioxol hydrochloride (Compound No. 7 in Table 1)

The procedure in Example 1 was repeated except that 5-(5-aminopentyloxy)-1,3-benzodioxol was employed in place of 5-(3-aminopropoxy)-1,3-benzodioxol to obtain the title compound. M.p. 169°–173° C.

$^1$H-NMR (DMSO-d$_6$) δ 9.10 (2H, m), 6.88 (4H, m), 6.78 (1H, d, J=8.5 Hz), 6.60 (2H, d, J=2.5 Hz), 6.34 (1H, dd, J=8.3, 2.5 Hz), 5.93 (2H, s), 4.65 (1H, m), 4.36 (1H, dd, J=11.5, 2.3 Hz), 4.04 (1H, m), 3.88 (2H, t, J=6.2 Hz), 3.20 (2H, m), 2.98 (2H, m), 1.71 (4H, m), 1.44 (2H, m).

Preferred compounds (I) of the present invention include those listed in Table 1 below as well as Compound Nos. 1, 4 and 7 as mentioned above.

TABLE 1

| Compound No. | Position | m | n |
|---|---|---|---|
| 1 | m | 3 | 1 |
| 2 | m | 3 | 2 |
| 3 | m | 3 | 3 |
| 4 | m | 4 | 1 |
| 5 | m | 4 | 2 |
| 6 | m | 4 | 3 |
| 7 | m | 5 | 1 |
| 8 | m | 5 | 2 |
| 9 | m | 5 | 3 |
| 10 | m | 2 | 1 |
| 11 | m | 2 | 2 |
| 12 | m | 2 | 3 |
| 13 | o | 3 | 1 |
| 14 | o | 3 | 2 |
| 15 | o | 3 | 3 |
| 16 | o | 4 | 1 |
| 17 | o | 4 | 2 |
| 18 | o | 4 | 3 |
| 19 | o | 5 | 1 |
| 20 | o | 5 | 2 |
| 21 | o | 5 | 3 |
| 22 | o | 2 | 1 |
| 23 | o | 2 | 2 |
| 24 | o | 2 | 3 |

EXAMPLE 4

Affinity of the compounds (I) or (II) of the present invention to 5-HT$_{1A}$ receptor was determined according to a binding assay using 8-hydroxy-2-(di-n-propylamino)tetralin (referred to as [3H]8-OH-DPAT hereinafter), which is a selective ligand to 5-HT$_{1A}$ receptor (Neuropharmacol. 26, 139, 1987). Thus, rat brain was homogenized in Tris-HCl buffer and centrifuged. The resultant precipitates were homogenized again with Tris-HCl buffer and incubated at 37° C. for ten minutes. The mixture was centrifuged again, and the precipitates were homogenized with Tris-HCl buffer containing pergiline, calcium chloride, and ascorbic acid to obtain a membrane preparation for use in the binding assay.

The preparation was mixed with [3H]8-OH-DPAT and a compound to be tested, and incubated at 37° C. for 10 minutes, filtered with whatman GF/B filter. Radioactivity remaining on the filter was measured by liquid chromatography.

Affinity of the test compound to 5-HT$_{1A}$ receptor is represented by Ki value which is calculated from the following equation.

$$Ki = \frac{IC_{50}}{1 + \frac{[L]}{Kd}}$$

wherein [L] is the concentration of [3H]8-OH-DPAT, Kd is a dissociation constant, and IC$_{50}$ is the concentration of the test compound requisite for attaining 50% inhibition of the binding of [3H]8-OH-DPAT. A lower Ki value represents a higher affinity of the test compounds to 5-HT receptor and therefore usefulness of the compounds as an antianxiety agent.

The test results are summarized in Table 2.

TABLE 2

| Compounds | Salt form | Ki value (nM) |
|---|---|---|
| No. 1 (dl) | HCl | 1.6 |
| (S) | HCl | 0.29 |
| (R) | HCl | 3.9 |
| No. 2 (dl) | HCl | 2.5 |
| No. 3 (dl) | HCl | 7.6 |
| No. 4 (S) | HCl | 0.91 |
| No. 6 (dl) | HCl | 2.9 |
| No. 7 (dl) | HCl | 4.09 |
| (S) | HCl | 1.84 |
| No. 13 (dl) | HCl | 9.7 |
| Buspirone (Active Control) | | 14 |

Table 2 shows that the compounds of the present invention possess a higher 5-HT$_{1A}$ receptor-binding ability than Buspirone, a known antianxiety agent, and therefore, it is highly expected that they should be excellent antianxiety agents.

EXAMPLE 5

The conflict test was performed to examine the anxiolytic activity of compounds. A modification of the method of Vogel et al (Psychopharmacology 21, 1, 1971) was used.

Rats were deprived of water for 38 hours prior to the first training session (unpunished session). Each animal was placed in a conflict test apparatus. The rat was allowed to drink water through a spout and the frequency of drinking action within 10 min was counted. Only rats making more than 100 licks progressed to a further 24 hr deprivation of water. Twenty four hours after the unpunished session, the rat was placed again in the test box. The second session (pre-drug punished session) consisting of a 3 min period started when the rat completed 20 licks and received the first electric shock. After every 20 unpunished licks, subsequent licking was punished. Only rats in which the number of receiving the shocks was reduced by at most 25 times during the pre-drug punished session were included in the test.

The compound to be tested was orally administered to each rat. One hour after the administration, the rat was re-placed in the apparatus to be examined. The number of shocks was counted for three minutes. Buspirone, an anxioselective anxiolytic drug, was used as a positive control.

The results are shown in the following Table 3. The anti-conflict activity was evaluated to be positive when the number of shocks in the treated group was higher than that in the control group.

TABLE 3

| Compound | | Dose (mg/kg) | Frequency of receiving the shocks (times/3 minutes) |
|---|---|---|---|
| Control | | | 7.4 |
| No. 1 | (dl) | 0.25 | 20.9 |
| | (S) | 0.05 | 20.1 |
| | (R) | 0.5 | 12.5 |
| No. 2 | (S) | 0.2 | 21.8 |
| No. 3 | (S) | 0.2 | 18.0 |
| Buspirone | | 5.0 | 14.4 |

Acute Toxicity

The compounds (I) suspended in 0.5% CMC-Na aqueous solution were orally administered to male and female rats, and 7-days observation was conducted. ALD (approximate lethal dose) value for Compound No. 1 was 100 mg/kg (p.o.).

EXAMPLE 6

(1) Tablets

The following components were mixed and pressed into tablets according to a conventional method.

| Compound No. 1 (S) | 10 mg |
|---|---|
| Crystalline Cellulose | 21 mg |
| Corn Starch | 33 mg |
| Lactose | 65 mg |
| Magnesium Stearate | 1.3 mg |

(2) Soft Capsules

The following components were mixed well and filled into capsules in conventional manner.

| Compound No. 1 (S) | 10 mg |
|---|---|
| Olive Oil | 105 mg |
| Lecithin | 6.5 mg |

(3) Injections

The following components were mixed well and charged into 1 ml ampules.

| Compound No. 1 (S) | 0.7 mg |
|---|---|
| NaCl | 3.5 mg |
| Injectable Distilled Water | 1.0 ml |

What is claimed is:

1. 5-[3-{(2S)-(1,4-Benzodioxan-2-ylmethyl)amino}-propoxy]-1,3-benzodioxol or an acid addition salt thereof.

2. 5-[3-{(2S)-(1,4-Benzodioxan-2-ylmethyl)amino}-propoxy]-1,3-benzodioxol hydrochloride.

3. A pharmaceutical composition for treating anxiety which comprises as an essential component an effective amount of 5-[3-{(2S)-(1,4-Benzodioxan-2-ylmethyl)amino}-propoxy]-1,3-benzodioxol or an acid addition salt thereof together with a suitable excipient or carrier therefor.

4. The composition according to claim 3 wherein the essential component is 5-[3-{(2S)-(1,4-Benzodioxan-2-ylmethyl)amino}-propoxy]-1,3-benzodioxol hydrochloride.

* * * * *